United States Patent [19]

Bagnall et al.

[11] Patent Number: 4,564,363
[45] Date of Patent: Jan. 14, 1986

[54] DELAYED ACTION ASSEMBLY

[75] Inventors: Brian G. Bagnall, Berwyn; Robert J. Gyurik, Downingtown, both of Pa.

[73] Assignee: SmithKline Beckman Corporation, Philadelphia, Pa.

[21] Appl. No.: 513,512

[22] Filed: Jul. 13, 1983

[51] Int. Cl.$^4$ .............................................. A61M 31/00
[52] U.S. Cl. .................................... 604/891; 604/890; 604/93; 604/140; 222/641
[58] Field of Search ................ 604/890, 891, 93, 131, 604/140–143, 145, 403; 128/630, 631; 222/3, 5, 638, 639, 641, 644, 642; 102/215, 367, 368

[56] References Cited

U.S. PATENT DOCUMENTS

| | | |
|---|---|---|
| 3,056,724 | 10/1962 | Marston . |
| 3,308,818 | 3/1967 | Rutkowski ........................... 604/403 |
| 3,340,866 | 12/1967 | Nöller ................................. 128/631 |
| 3,399,468 | 9/1968 | Gahle .................................. 102/367 |
| 3,507,952 | 4/1970 | Rednick et al. . |
| 3,636,874 | 1/1972 | Gey et al. ............................ 102/367 |
| 3,788,322 | 1/1974 | Michaels ............................. 604/890 |
| 4,066,019 | 1/1978 | Mennert .............................. 102/215 |
| 4,094,028 | 6/1978 | Fujiyama et al. ...................... 222/3 |
| 4,326,522 | 4/1982 | Guerrero et al. ...................... 604/57 |
| 4,353,301 | 10/1982 | Jacobsen ............................. 102/368 |
| 4,425,117 | 1/1984 | Hugemann et al. ................. 604/890 |
| 4,439,197 | 3/1984 | Honda et al. ........................ 604/891 |

FOREIGN PATENT DOCUMENTS 1117825 11/1961 Fed. Rep. of Germany .

OTHER PUBLICATIONS

Chem. Abst. 76 108074K (1972).

Primary Examiner—C. Fred Rosenbaum
Assistant Examiner—Mario Costantino
Attorney, Agent, or Firm—William H. Edgerton; Richard D. Foggio; Alan D. Lourie

[57] ABSTRACT

A device for effecting the delayed release of an active ingredient comprises a container and, within, a dispersible unit of ingredient, a removable closure and a electrical control circuit for removal of said closure at a designated time to release the active ingredient. Several assemblies are combined to control the administration of veterinary medicaments to ruminant animals as a specific application of the invention.

8 Claims, 16 Drawing Figures $0 + t_1 \rightarrow$ $t_1 \rightarrow$ $t_1 + t_2 \rightarrow$ $t_2 \rightarrow$

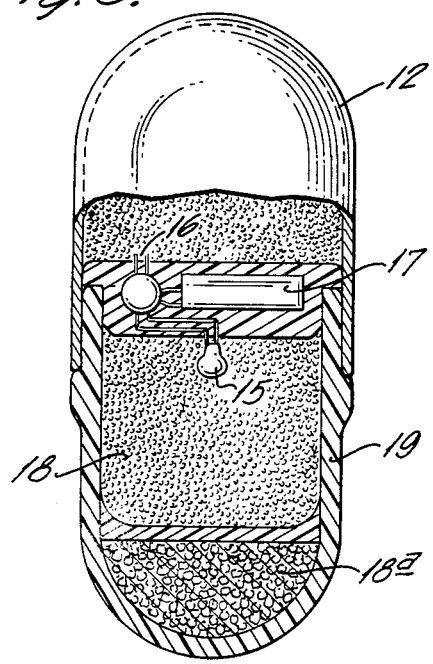
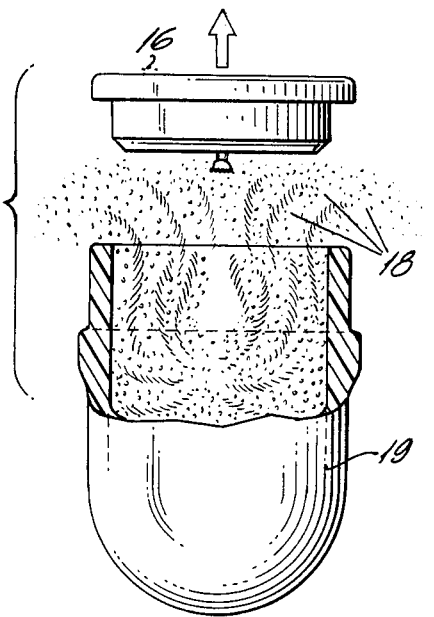
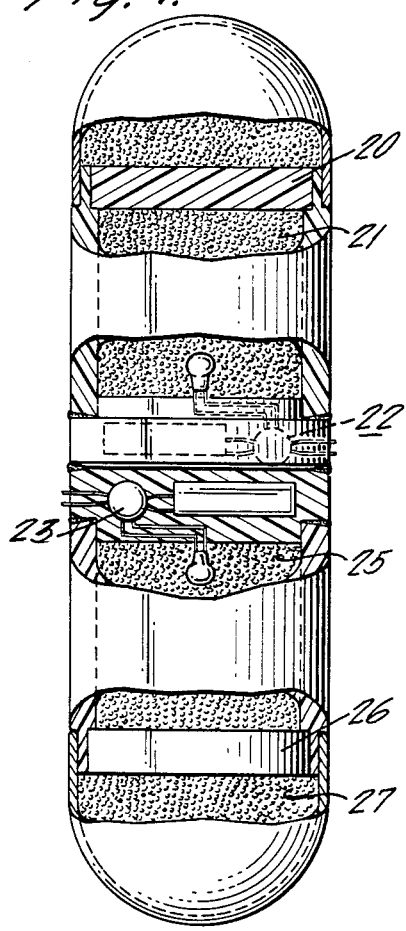
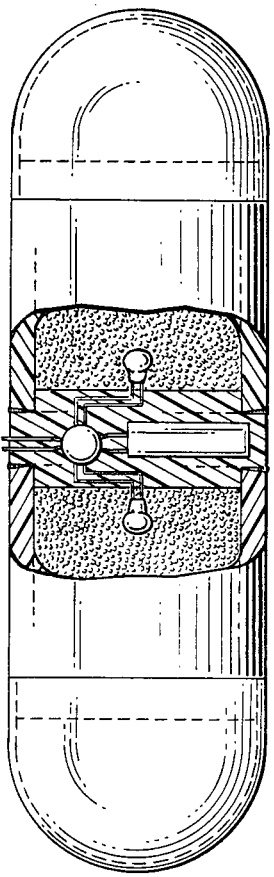
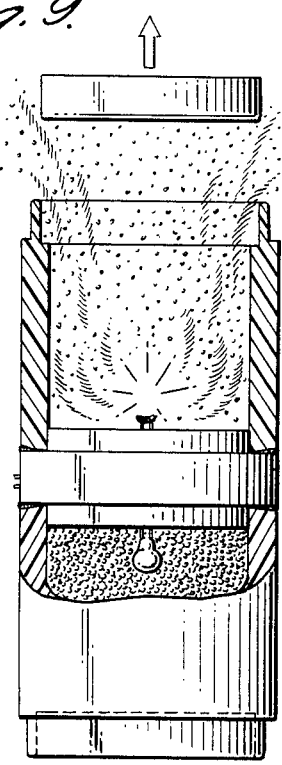

DELAYED ACTION ASSEMBLY

This invention relates to a new delayed action assembly which is useful for controlling the release of active ingredients, for example, medicaments, diet supplements or growth promotants in ruminants such as cattle, sheep or goats. This invention also comprises a delivery device which releases an initial quantity of an active ingredient followed by the release of additional quantities, on a preset time schedule, by the use of one or more of the delayed action assemblies described in more detail hereinafter.

BACKGROUND OF THE INVENTION

The use of boluses in the treatment of ruminants is well known in the veterinary field. Such products are often weighted by a heavy density substance, such as iron or sand, in order to remain in the rumen to release a medicament. If sustained release coatings are present, the release is gradual until the source of medicament is exhausted. Exemplary of such prior art practices are German Patent No. 1,117,825, U.S. Pat. Nos. 3,507,952 or 3,056,724 and Chem. Abst. 76 108074K (1972).

While the delayed action assembly of the present invention resembles a ruminant bolus since it is designed to control the release of an active ingredient while remaining in the rumen in its most important embodiment, applicants believe this new delayed release assembly and devices containing it are distinct in both structure and function over this art.

BRIEF DESCRIPTION OF THE DRAWINGS

FIG. 5 is a semi-schematic, side elevational view, partially in section, of a modified device which has an immediate release and a delayed release action.

FIG. 6 is a side elevational view, partially in section, of the non-biodegradable portion of the delayed action device of FIG. 5, in a firing mode.

FIGS. 7 and 8 are semi-schematic, side elevational views of additional modifications of a delayed action device with portions broken away to show details of assembly.

FIG. 9 is a side elevational view, partially in section, of the non-biodegradable portion of the delayed action device of FIG. 8 in which one delayed action assembly is in a firing mode.

DESCRIPTION OF THE INVENTION

Figure 1:
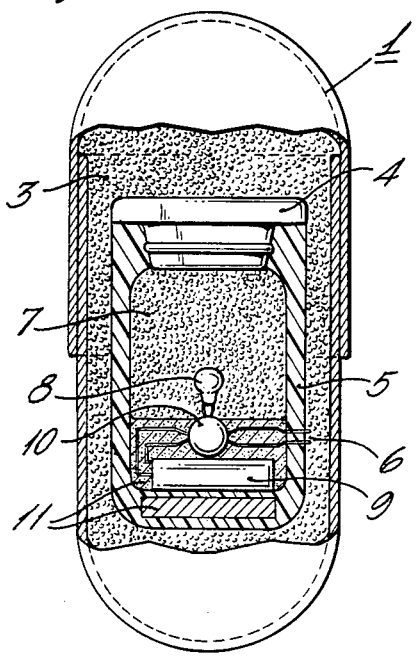
FIG. 1 is a semi-schematic, side elevational view of this invention embodied in a delayed action ruminant bolus, with parts broken away and in section, to illustrate the use of a single delayed action assembly.

This invention comprises an assembly for releasing measured quantities of an active ingredient. One embodiment of the invention releases an active ingredient, which is useful in the ruminant art, within the rumen and, then, at optionally varied intervals, releases additional doses into the same milieu. The release regimen for an active ingredient using this invention, therefore, comprises the release of a series of standard dosage units of the active ingredient in timed, delayed increments rather than in a sustained release pattern. This allows an effective treatment to be spread over a longer time span per space of dosage unit than many of the prior art sustained release products.

One example of such a product form (FIG. 1) comprises a capsule-like container and dispersed therein an immediate dose of active ingredient 3 and one or more delayed action assemblies 4–10. The wall of the outer container of this device is comprised of a biodegradable polymeric material, which is known to the pharmaceutical art, such as hard gelatin, soft gelatin or water soluble cellulosic derivatives such as methylcellulose, ethylcellulose or sodium carboxymethylcellulose. The term "biodegradable", as used herein, means a material which is either soluble in the rumen or otherwise readily disrupted by rumen content so the immediate dosage unit and delayed action assemblies are released.

This container holds a dosage unit of active ingredient 3 which is available for initial release and, as noted above, another dosage unit in a delayed release assembly of this invention for timed release of a second unit of the active ingredient. The ingredient in each initial or delayed release dosage unit is in powder, granule or slug form and must be either readily soluble or easily dispersible by the use of various pharmaceutical aids.

Such aids include pharmaceutical fillers such as kaolin, mannitol, a powdered or granulated sugar, dicalcium phosphate, starch, microcrystalline cellulose, lactose or calcium phosphate; binders such as gelatin, gums or sugars; lubricants such as a metal stearate, a fatty acid, talc, graphite or cocoa butter; or granulating agents such as zein, acacia, tragacanth, gelatin, sodium alginate, a cellulosic derivative or magnesium stearate.

Disintegrators or wicking agents, which are used in the pharmaceutical art for granulations or tablets, are particularly useful for insuring that the active ingredient will be expelled from either an initial or a delayed release compartment, the latter after the displaceable cover of the delayed release assembly is displaced by an internal removal means. Such compounds include potato starch, cornstarch, "Veegum HV", methylcellulose, agar, bentonite, sponge material, cation-exchange resins, alginic acid, guar gum, citrus pulp, carboxymethylcellulose and, especially, sodium starch glycolate. Other agents, such as carbon dioxide generating agents, for example sodium bicarbonate-citric acid, may also be used. The disintegrator is present in from 2-10% by weight of formulation which contains the active ingredient. The non-active substances are kept at a minimum.

Figure 2:
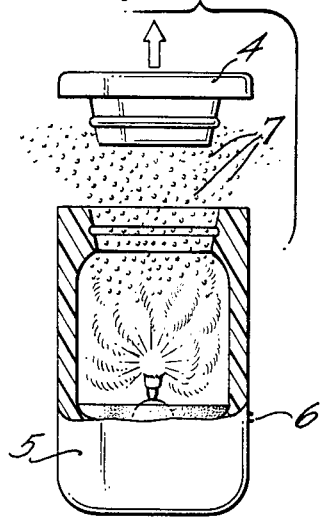
FIG. 2 is a semi-schematic, side elevational view, partially in section, of the delayed release assembly portion of FIG. 1 which is shown in a firing mode.

The delayed release assembly of this invention is exemplified by components 4-10 of FIG. 1. Each of 6-10 is contained in a non-biodegradable container 5 which is usually formed in a capsular or cylindrical shape having an opening. The opening is closed with a water tight but easily removable closure 4, such as a diaphragm, plug, cap or cover. FIG. 2 is an action diagram of the delayed action assembly in the process of releasing an active ingredient.

The outer dimensions of each delayed release assembly are, for example, from 1-5 inches in length, ½ to 2 inches in diameter with about a 1/16 to ½ inch wall thickness. Preferably, the overall size will be about 2" by 1". A whole bolus for ruminant application will be from 2-6 inches in length by 1-3 inches in diameter. The size of the product form is dictated by the number of doses and the application for which the delayed release of an active ingredient is to be used.

The non-biodegradable container wall 5 and removable closure 4 are comprised, preferably, of a high molecular weight polyethylene or polypropylene polymer. Also, a silicone elastomer may be used, such as "Silastic" Dow-Corning Corporation, Midland, Mich. 48640. Alternative wall materials are soft polystyrene, polycarbonate, polyvinylchloride, polysulfone, polymethylpentene or polyimide polymers. Non-organic materials include a corrosion resistant metal such as stainless steel, a ceramic or a non-friable glass. The term "non-biodegradable" is used to indicate that the wall material is resistant to its target milieu, for example the rumen environment, over the desired time of ingredient release. Of course, the container wall must be impervious to the target liquid during the release cycle.

The outer shell 5 of the delayed release assembly is fabricated as known in the art into the chosen shape, usually a capsule or bolus-like cylinder. For example, when the preferred polymers are used, injection molding is convenient.

Figure 3:
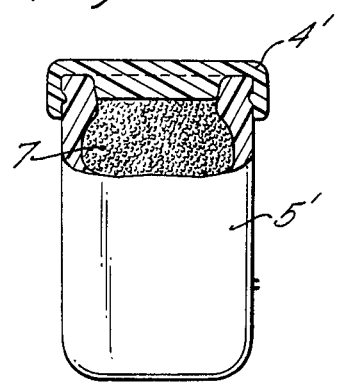
FIG. 3 is a side elevational view, partially in section, showing a modified water tight plug for the delayed release assembly of FIGS. 1 and 2.

The removable closure 4 is usually made of the same material as that used for the outer wall but must be liquid tight and easily removed by internal pressure. It may be grooved to snap into place as shown in FIGS. 1 and 2. Other closures, such as a diaphragm, may be held in place with adhesive or light crimping. At times, the cap or plug may have a lower durometer or hardness reading than that of the wall material. Normally, the closure is a simple cylindrical plug which is kept in place by external liquid pressure and adhesion to the container opening. The plug may contain most of the components of the pressure generating circuit, see FIGS. 5 and 6. An internally arranged closure is illustrated by FIG. 2, an externally arranged closure is illustrated by FIG. 3.

Ingredient 7 comprises one or more active ingredients which are combined with optional dispersants, disintegrators, fillers, granulation agents or lubricants as discussed above. If the active ingredient is difficultly water soluble, the particle size of the active ingredient is to be such that medicament 7 will be expelled forcefully through the vacated opening of the assembly into the target area upon firing. The ingredient 7 may be in the form of a powder, slug, granule, sustained release granule or mini-bolus.

Weight means 11 comprises added heavy density material such as sand, bentonite, iron pellets or filings, glass pellets, heavy metal salts such as calcium sulfate dihydrate, cementitious matter or clay balls. Such are optionally used when the assembly should be more dense than the liquid medium into which the active ingredient is to be released and when the device is intended to remain as targeted. The weight means may be either incorporated into a wall 5 or distributed with the active ingredient 7. The weight means in a delayed action bolus for ruminants should be sufficient to enable the assembly to remain in the rumen sack throughout the treatment period by itself or as part of the complete bolus which has already released earlier units of active ingredient. The entire unit or each delayed action assembly, as the case may be in ruminants, will have a density of about 1.5-5.0, preferably 2.0-3.0, which is sufficient to retain the delivery device in the rumen until the period of drug delivery is complete. The weight means is not an essential part of the assembly for all applications.

Figure 4A:
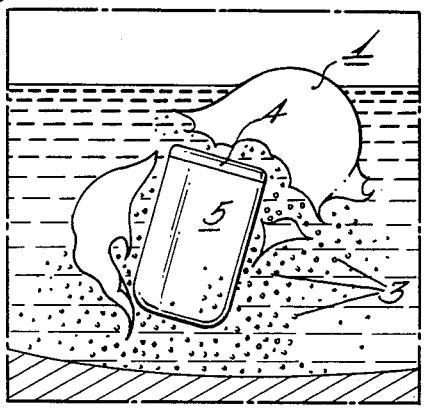
FIGS. 4A→4D are sequential views illustrating schematically the manner of operation of this invention for a delayed release of an active ingredient from the bolus of FIG. 1.
Figure 4B:
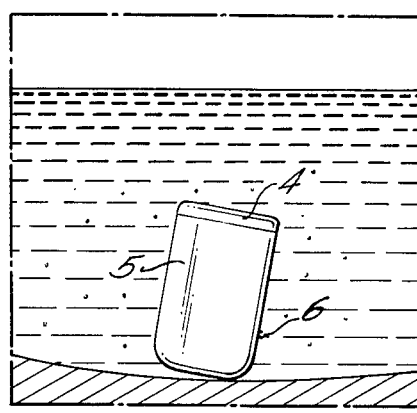
Figure 4C:
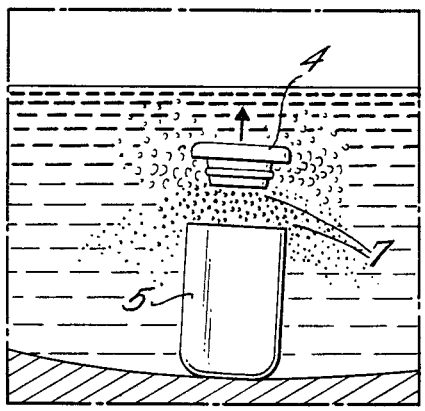
Figure 4D:
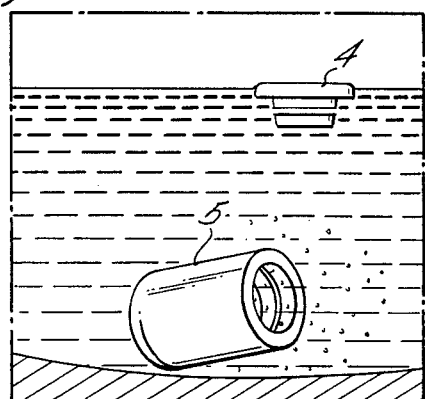

FIGS. 4A→4C represent the working mode of the embodiment of this invention represented by FIG. 1 which comprises a single delayed release assembly enclosed in a gelatin capsule. 4A represents the splitting of the biodegradable coating after reaching the target area ($t_1$). 4B represents the resting state of the delayed assembly during which the timing function is active ($t_r$) such as 30 days. 4C represents the controlled firing of the delayed dose. 4D represents the expended casing of the assembly.

Each separate delayed release assembly for rumen application may, optionally, contain a hydrocolloid or another swellable material which, after expulsion of the medicament and being in touch with the liquid rumen fluid, will expand into the vacated interior space of the dosage unit. The lightened unit will then rise to the top of the rumen fluid and may pass away. This mechanism is especially effective if the weight means is dispersed with the medicament composition. Alternatively, without such a flotation capability, the dosage unit will remain in the rumen until the animal is marketed.

Figure 13:
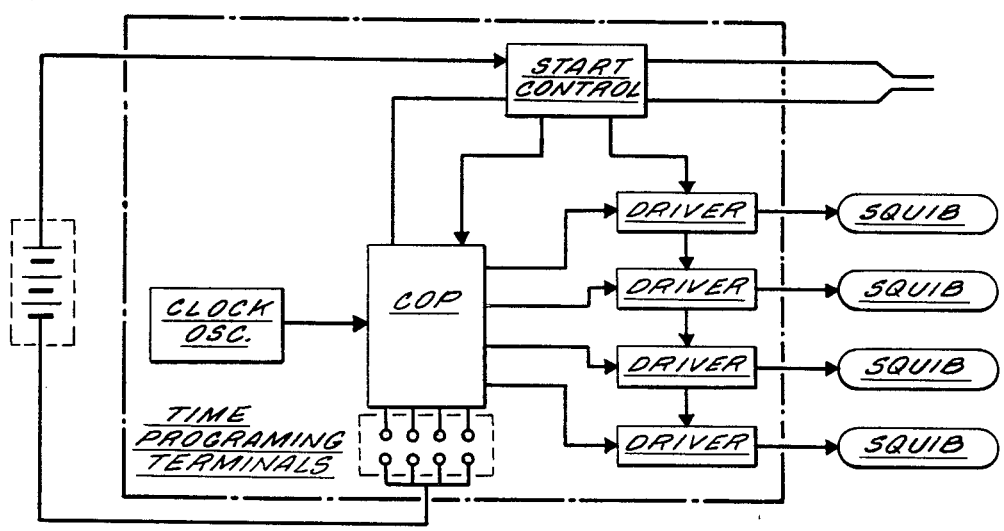
FIG. 13 is a schematic block diagram showing components of the microcircuit utilized to time and provide the delayed electrical impulse to trigger the pressure release mechanism, unplug the non-biodegradable, delayed action assembly and release the active ingredient therefrom. The broken rectangle contains the elements of the microcontroller for the timing-release function adapted to fire four closure release means.

A distinguishing portion of the delayed release assembly of particular interest is an electrical circuit (6, 8, 9 and 10 of FIG. 1) used to time and, then, to fire in order to generate internal pressure within the delayed release assembly to force out the removable closure means 4, thereby, releasing the delayed unit of active ingredient at will. FIG. 13 represents the external and internal components of the circuit. This circuit exerts the necessary internal pressure by release of gas within the container such as by using a squib or electric match or by mechanical pressure against the closure from within such as by using a spring-rod mechanism.

One such pressure generating means 8 comprises a chemical squib or match which is available in other arts. Such pyrotechnic devices are supplied by ICI Americas Inc., Valley Forge, Pa. 19482. The squib reacts upon contact with heat from an internal, high resistance wire. The heat is generated by an electrical current to explode the detonating charge with release of gas and heat within the assembly. A potential of 1.5 to 3 volts plus sufficient current is used to activate such a squib. Non-toxic chemical ingredients and residues are preferred for use in the squib, however, the quantity of by-products released after firing is very small which gives considerable leeway to the type of squib usable.

As a specific example of a squib means 8, a bead of about 5–20 mg of 90% potassium dinitrobenzofuroxan (PDBF) coated with nitrocellulose lacquer is fired by current passing through a nichrome wire with a resistance of 1–10 Ohms with a current of 0.5 amps for five milliseconds. A squib of barium styphnate is another example of a satisfactory pressure generating means.

An alternative is a mechanical device comprising a tube containing a rod in contact with the removable cover means 4 which is connected with a compressed spring, at least at the lower end of the rod. The spring is maintained in a compressed state by a noncorrosive metal or alloy which has a melting point above the temperature of the target milieu, i.e. around 35°–100° C. or above the body temperature of the target species for a veterinary product, such as from 105°–115° F. Usually, a commercial solder such as a zinc alloy, a cadmium alloy and the like is used for the freezing metal. Electric power is applied as described above to melt the metal or plastic, holding or freezing means, thereby, releasing the spring which drives the rod against the closure means 4. The squib firing means is preferred because of the limited space available in the assembly.

The source of the current 9 in the timing-activating-firing circuit is connected to the pressure generating means 8 via timer-activator means, 10. Micro batteries or button batteries of the commercially available lithium, manganese or silver oxide types are used to generate the current in the circuit necessary for timing and firing the pressure generating means. Specific button batteries use generating systems such as manganese dioxide-zinc or silver oxide-zinc and containing an alkaline electrolyte and a 45% solution of potassium or sodium hydroxide. Examples of such batteries are electric watch, calculator or hearing aid batteries. The batteries are about 8 mm to 23 mm in diameter and up to 66 mm thick. Generally, as stated above, a battery which provides from about 1.5–4.0 volts is satisfactory. A requirement of the battery is to provide 25 microamps at 3 volts for the timing function.

The timing and pressure activating means 10 is an important part of the mini-circuit within the delayed release assembly of FIG. 1 which is designed to release multiple (1–12) timed release dosage units at the site of attack. Said means comprises a single chip microcontroller which is essentially a microcomputer containing system timing, internal logic, ROM and input/output necessary to implement the dedicated control functions to initiate the timing periods, then measure the time periods and direct sufficient energy from the battery means 9 to the pressure generating means 8 to trigger the release of an active ingredient. FIG. 13 represents the components within the timing and pressure activating means for a four unit activation system.

Such timing means are commercially available. Single chip CMOS microcontrollers such as "COPS" 411-C or 410-C (National Semiconductor Corporation) are useful because they draw negligible power for the counting function. The timing interval, for example, may be 10 minutes, 2 weeks, 4 weeks and 6 weeks or longer. Any time sequence, which is desired by the operator within the capacity of the battery means and the timing means, is obtainable by adjusting the programing terminals of FIG. 13 as known to the art.

Circuit activating means 6, in one embodiment, for initiating the current in the circuit of FIG. 1 is necessary to close the interconnected parts of the circuit and to begin the operation of the time delay program prior to or immediately upon ingestion by the animal. Said activator means may be a micro-switch for the electrical current which is activated or tripped by the operator prior to administration. A contact means such as a button, pull-tab or string connected to the switch-activator which closes the circuit is convenient. Such is usually imbedded into the plastic support for the delayed release firing assembly, especially when the assembly forms the bottom or the wall opposite the removable closure as described in FIGS. 10 or 12. The pull-tab must be affixed in the unit in water tight condition.

A preferred embodiment of the activator 6 for use in veterinary or similar applications is to run two wires of the circuit to the external surface of the bolus unit through the container wall in water tight fashion. Thusly, conductivity through the rumen fluid completes the circuit and activates the timing-firing sequence, then, optionally shuts off as designated such as after 10 minutes. The circuit powered by the battery then takes over operation to time and fire the pressure generating means.

The exposure of the activator wire to rumen fluid may be in any form, such as those described in FIGS. 1, 7, 8 or 10 as noted in FIG. 13. Using this preferred activator of the circuit circumvents the step of specifically activating the delayed release bolus by a conscious act since activation occurs spontaneously upon contact with a liquid which supports conductivity to activate the timer-firing sequence.

Each delayed release assembly may be, alternatively, activated by external radio frequency by using a microreceiver as an internal activator. In such devices, the receiver acts as switch means. Similar devices are used in the art to control remote detonation in blasting operations or to trigger marker dyes associated with bank funds upon illegal removal from the bank. Different radio frequencies can be used to control each firing, either within a multiple-head pressure generating device or among several devices.

FIG. 5 illustrates a variation of a veterinary device of this invention in which the immediate release ingredient, which is contained within biodegradable wall 12 and is attached to a portion of the delayed action assembly rather than surrounding it as is the case in FIG. 1. The bottom part of the container is comprised of non-biodegradable wall material 19 with dispersible medicament 18 therein, optionally admixed with weights. The control release circuit, comprised of the activator 16, battery and timer 17 and means for generating internal pressure 15, is sealed in an inert plastic material. This plastic body forms the wall between the immediate and delayed release ingredient chambers. Said body which contains the release circuit also forms the removable plug capable of release upon generation of pressure within the lower or time delay chamber by the circuit. In general, the internal units of the timing-firing mechanism may be imbedded, usually in plastic, as the plug means of FIG. 6 or as the wall or end opposite the plug means.

The described units may be combined in a cylindrical container having rounded or non-irritating ends as in FIG. 7 which have two plugs 20 and 26, three dosage unit cavities 21, 25 and 27, and two single event timing compound release assemblies, 22 and 23, the latter each including an exposed wire circuit activator as described above. The two single event timing and release assemblies which are glued to the container walls may be replaced with a single two event, or gemini, timer assembly. Use of this variation of the invention gives a roman candle-like release of medication at desired time intervals. The walls of the cylinder are made of non-biodegradable material. One or both of the end walls may be made of degradable material. FIG. 8 depicts the use of a gemini firing assembly for removing opposite closures at different times. FIG. 9 represents the first firing mode.

Figure 10:
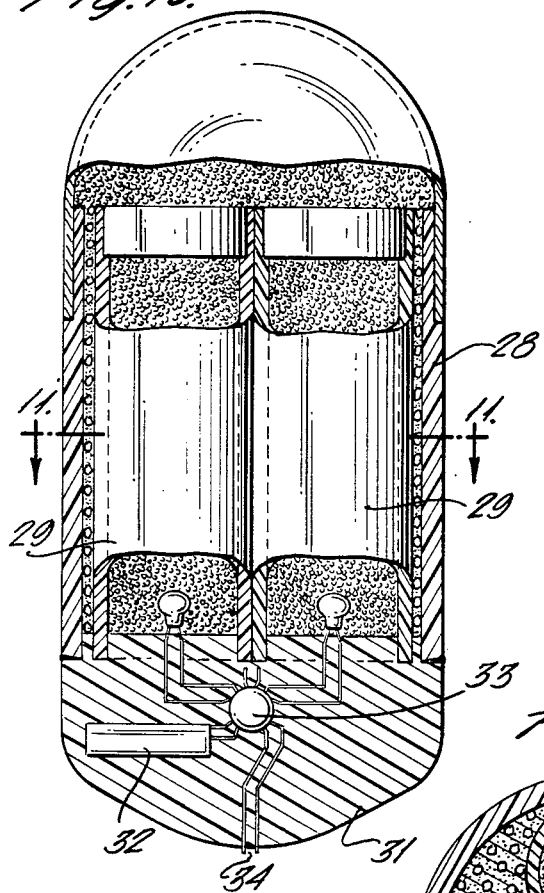
FIG. 10 is a semi-schematic, side elevational view, partially in section, of still another modification for a release device with side by side delayed action assemblies having a gemini circuit system.
Figure 12:
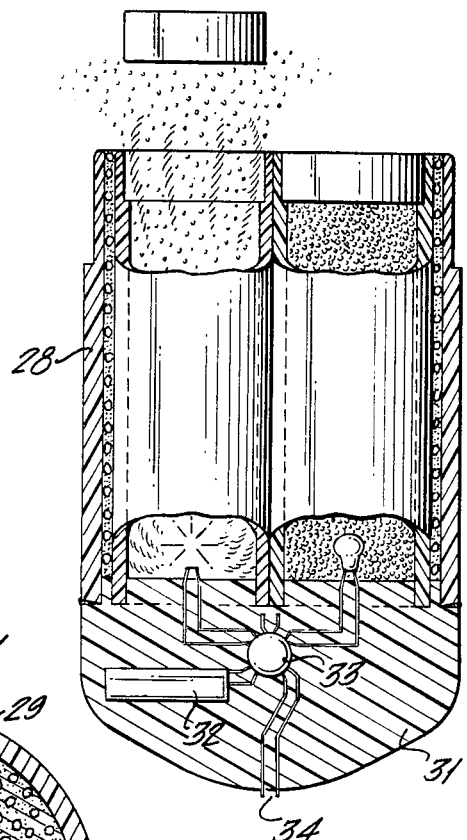
FIG. 12 is a sectional side elevational view of a multiple delayed action assembly, one chamber of which is in a sequential firing mode.
Figure 11:
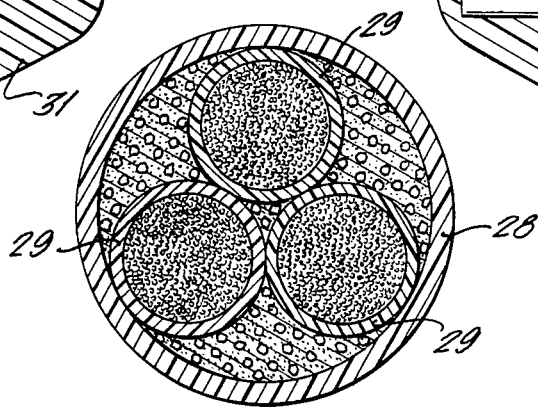
FIG. 11 is a sectional plan view taken on the line 11, 11 of FIG. 10 showing a three chambered release device.

A second modification is to combine units side by side to give a missile-like release at preset times as in FIG. 10 or 12. A rigid plastic tube, 28, is set with three firing tubes, 29, each with a removable plug and a triple event timing and release assembly (32, 33 and 34) or three single event units, one of which may optionally be used for immediate release. Weights or immediate release medicament may be added between the tubes. The exposed wire type of circuit trigger, 34, is useful for this assembly. FIG. 12 represents the first firing mode of a three chambered embodiment. This device does not necessarily use an immediate release of the active ingredient which is controlled by the dissolution of a cylinder wall. The embodiment of FIG. 10 contains the option for immediate release of an active ingredient when a partial gelatin wall is used. In both FIG. 10 and 12, the third release asembly is below the plane of the paper as noted by a cross section as in FIG. 11.

Any medicament or growth promotant which an operator desires to administer to ruminants such as cattle, sheep or goats in a discrete number of doses over a period of time are suitable active ingredients for this invention. Most useful of the various ruminant active ingredients are anthelmintics such as albendazole, fenbendazole, oxfendazole, ivermectin, thiabendazole, mebendazole, cambendazole, pyrantel, morantel or levamisole; antibiotics such as streptomycin, virginiamycin, a vancomycin-like glycopeptide, a tetracycline or an ionophore; sulfa drugs especially sulfamethazine; trace metal necessary for metabolism such as selenium, copper, zinc or cobalt; vitamins; or oral vaccines useful in the veterinary field.

It will be understood by one skilled in the art that the active ingredient, if not readily water soluble, should be prepared in a readily dispersed form prepared as known to the art and as described herein. This does not mean that, to solve a particular need, a slug or minibolus unit will be inoperative for use in animals.

A typical dispersive medicament preparation in the form of a dosage unit, which is useful for charging an active ingredient chamber of a ruminant device, comprises finely divided albendazole (1.92 g), polyoxyethylene(20)sorbitan monooleate (0.06 g) and "Centrophase C" (0.2 g and which is lecithin plus a wetting agent). Another composition contains albendazole powder 70.0% w/w, magnesium stearate 1.0%, starch 8.0% and dicalcium phosphate dihydrate, 21%. One of either of these dosage units is charged into each chamber of a three-chambered unit of FIG. 12 which is set to be released at 10 minutes, 30 days and 60 days. The bolus unit is then administered to cattle which are infected, or liable to infection, with nematodes.

The prime purpose of this aspect of the invention is to achieve a repeat action of the medicament by periodic release of dosage units in the rumeno-reticular sac of ruminants rather than a sustained release of medicament as known to the art. The latter type of drug action is, however, easily obtained in the devices and sub-assemblies of this invention by using sustained release slugs, pellets or granules, prepared as known to the art, in the medicament chambers of the bolus of this invention.

Further, the delayed action assembly, such as that of FIG. 12, can be used to release other active ingredients such as fertilizers, insecticides, molluscacides, antibacterials, algicides or non-ruminant medicaments. Release of ingredient in aquatic surroundings such as to treat eutrophicated lakes with herbicides is another aspect of this invention.

What is claimed is:

1. A delayed release, ruminant dosage form comprising from 1 to 4 dosage unit release assemblies, at least one of which is a delayed action assembly which, in turn, comprises;
   a closed, non-biodegradable outer wall;
   a dosage unit of an active ingredient in dispersible form within said wall;
   a water-tight cover or plug which is capable of being displaced by internal gas pressure and which extends through said outer wall;
   weight means sufficient to retain said delayed action assembly in the rumen and arranged within said dosage form, and
   an internally disposed electrical circuit means which, in turn, comprises, interconnected;
      a source of current;
      an internally disposed chemical squib for generating internal gas pressure, within the assembly, sufficient to remove said removable cover or plug;
      means for timing and activating said chemical squib, and
      means for activating said circuit.

2. The dosage form of claim 1 in which the chemical squib is comprised of barium styphnate.

3. The dosage form of claim 1 in which the means for activating the electrical circuit is two wires completing the conductivity circuit by means of reumen content, said wires being exposed to said rumen content on the surface of the form.

4. The dosage form of claim 1 in which the non-biodegradable wall material is a polyethylene of polypropylene polymer.

5. The dosage form of claim 1 in which the active ingredient is an anthelmintic.

6. The dosage form of claim 1 in which the active ingredient is albendazole.

7. The dosage form of claim 1 for release of an active ingredient, in which said electrical circuit means comprising a source of current, which is sufficient to activate and operate said timing means and said chemical squib, as well as a switch means for activating said electrical circuit means are all disposed within said assembly.

8. The dosage form of claim 1 in which three assemblies are present, each timed to release its active ingredient at a preset period.

* * * * *